US00PP09331P

United States Patent [19]

Zaiger et al.

[11] Patent Number: Plant 9,331

[45] Date of Patent: Oct. 17, 1995

[54] PLUM TREE 'BLUE GUSTO'

[76] Inventors: Chris F. Zaiger, 929 Grimes Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 369,589

[22] Filed: Dec. 30, 1994

[51] Int. Cl.[6] ..... A01H 5/00

[52] U.S. Cl. ..... Plt./38.1

[58] Field of Search ..... Plt./38.1

*Primary Examiner*—James R. Feyrer

[57] ABSTRACT

A new and distinct variety, of plum tree whose novelties consist of the following unique combination of features that are desirable in a new plum variety:

1. Late maturity of large size fruit.
2. Fruit with excellent flavor and eating quality.
3. Fruit with firm flesh, good handling and shipping quality.
4. Fruit with an attractive dark blue skin color.
5. Regular and heavy production of fruit.
6. Vigorous upright growth.

1 Drawing Sheet

ORIGIN OF THE VARIETY

The present new variety of plum tree was originated by us in our experimental orchard located near Modesto, Calif., as a first generation cross between two selected plum seedlings with the identification numbers 26GB440 and 105GD60. The maternal parent 26GB440 originated from a cross between King David Plum (non-patented) and the selected seedling 46G452, which originated from a cross between Queen Ann Plum (non-patented) and Casselman Plum (non-patented). The pollen parent 105GD60 originated from a cross between Friar Plum (non-patented) and the selected seedling 59GA511 which originated from a cross between Mariposa Plum (U.S. Plant Pat. No. 111) and Ebony Plum (U.S. Plant Pat. No. 2,049). A large group of seedlings from this first generation cross of 26GB440 by 105GD60 were grown and maintained under close observation by us. The present variety exhibited the desirable characteristics described above and was selected for asexual reproduction and commercialization.

ASEXUAL REPRODUCTION OF THE VARIETY

The present new variety of plum tree was asexually reproduced by budding, as performed by us, in our experimental orchard located near Modesto, Calif., which shows that all characteristics are established and transmitted through succeeding propagations.

SUMMARY OF THE VARIETY

This new and distinct variety of plum tree is large, vigorous, upright in growth. It is a regular and productive bearer of large, firm, clingstone fruit with excellent flavor and eating quality. The fruit is further characterized by having firm flesh, good storage and shipping quality, hanging firm on the tree 2 weeks after maturity (shipping ripe) and ripening in the late maturity season. In comparison to one of its parents, the Casselman Plum (non-patented), which ripens in the same maturity season, the fruit is larger in size, is dark blue instead of red and has no skin cracking.

BRIEF DESCRIPTION OF THE PHOTOGRAPH

The accompanying color photographic illustration shows typical specimens of the foliage and fruit of the new variety of plum tree. The illustrations are of the upper and lower surface of the leaves, and of the exterior and sectional view of the fruit that shows flesh coloration and a stone remaining in place. The photograph was taken shortly after the fruit was picked (firm ripe) and the colors are as nearly true as is reasonably possible in a color representation of this type.

DESCRIPTION OF THE VARIETY

The following is a detailed botanical description of the new and distinct variety of plum tree, its flowers, foliage and fruit, based on observations of specimens grown near Modesto, Calif. with color terminology (except those in common terms) in accordance with Reinhold Color Atlas by A. Kornerup and J. H. Wanschers.

Tree:
- *Size.*—Large.
- *Vigor.*—Vigorous.
- *Form.*—Upright.
- *Density.*—Medium dense.
- *Shape.*—Usually pruned to vase shape.
- *Productivity.*—Productive.
- *Bearing.*—Regular.

Trunk:
- *Size.*—Medium.
- *Texture.*—Medium shaggy.
- *Color.*—Brown to soot brown (5-E-4) to (5-F-4).

Branches:
- *Size.*—Medium.
- *Texture.*—Smooth to medium rough.
- *Lenticles.*—Medium number. Large size.
- *Color.*—Light brown to coffee brown (5-E-5) to (5-E-7).

Leaves:
- *Size.*—Large. Average length — 4¾". Average width — 1¾".
- *Form.*—Oblanceolate. Tip-acuminate.
- *Margin.*—Double serrate.
- *Thickness.*—Medium.
- *Texture.*—Smooth.
- *Petiole.*—Medium length. Medium thickness.
- *Glands.*—Globose. Number varies from 0 to 3. Average number 2. Size — small. Located on base of leaf blade and upper portion of the petiole.
- *Color.*— Upper surface — green to dark green (27-F-5) to (27-F-6). Lower surface — grayish green to green (28-E-5) to (28-E-7).

Flower buds:
- *Size.*—Small to medium.
- *Length.*—Medium.
- *Form.*—Plump. Free.

Flowers:

*Blooming period.*—Date of first bloom — Feb. 19, 1993. Date of full bloom — Feb. 25, 1993. Varies slightly with climate conditions.

*Size.*—Small to medium.

*Pollen.*—Present.

*Color.*—White.

Fruit:

*Maturity when described.*—Firm ripe.

*Date of first picking.*—Aug. 9, 1993.

*Date of last picking.*—Aug. 15, 1993.

*Size.*—Large. Average diameter axially — 3". Average diameter transversely in suture plane — 2⅝".

*Form.*—Ovoid. Flattened at stem end. Elongated at apex.

*Suture.*—Nearly smooth — extends from base to apex.

*Base.*—Retuse.

*Apex.*—Elongated — slightly more on suture side.

*Cavity.*—Rounded — slightly elongated in suture plane. Average depth — ⅜". Average breadth — ½".

*Stem.*—Medium length. Medium width.

Flesh:

*Ripens.*—Evenly.

*Texture.*—Firm.

*Fibers.*—Small — tender.

*Flavor.*—Excellent.

*Eating quality.*—Excellent.

*Juice.*—Moderate.

*Aroma.*—Very little.

*Color.*—Pale yellow to pastel yellow (2-A-2) to (2-A-4).

Skin:

*Thickness.*—Medium.

*Texture.*—Medium — tenacious to flesh.

*Tendency to crack.*—None.

*Down.*—Wanting.

*Bloom.*—Moderate.

*Color.*—Ground color — reddish brown (9-D-4) to (9-D-5). Overspread with bluish black to dull violet (17-E-3) to (18-F-5).

Stone:

*Type.*—Clingstone.

*Size.*—Medium. Average length — 1⅛". Average width — ¾". Average thickness — ⅜".

*Form.*—Ovate.

*Base.*—Mostly straight — some rounded.

*Apex.*—Acuminate.

*Sides.*—Mostly equal — varies from equal to unequal.

*Surfaces.*—Shallow furrows near stem end, with one long shallow furrow on each side of suture, pitted slightly throughout.

*Ridges.*—Narrow, small in size.

*Tendency to split.*—None.

*Color.*—Light brown to brown (6-C-5) to (6-D-5).

Use: Dessert.

*Market.*—Local and long distance.

Keeping quality: Good.

Shipping quality: Good.

The plum tree and its fruit herein described may vary in slightly detail due to climate, soil conditions and cultural practices under which the variety may be grown. The present description is that of the new variety grown under the ecological conditions prevailing near Modesto, Calif.

We claim:

1. A new and distinct variety of plum tree, substantially as illustrated and described, which is of large size, vigorous, upright in growth, and is a productive and regular bearer of large, late maturing, clingstone fruit with excellent flavor and eating quality; the fruit is further characterized by having firm flesh with good storage and shipping quality, holding firm on the tree for 2 weeks after maturity (firm ripe) and, in comparison to Casselman Plum (non-patented), is larger in size and does not have the skin cracking problems.

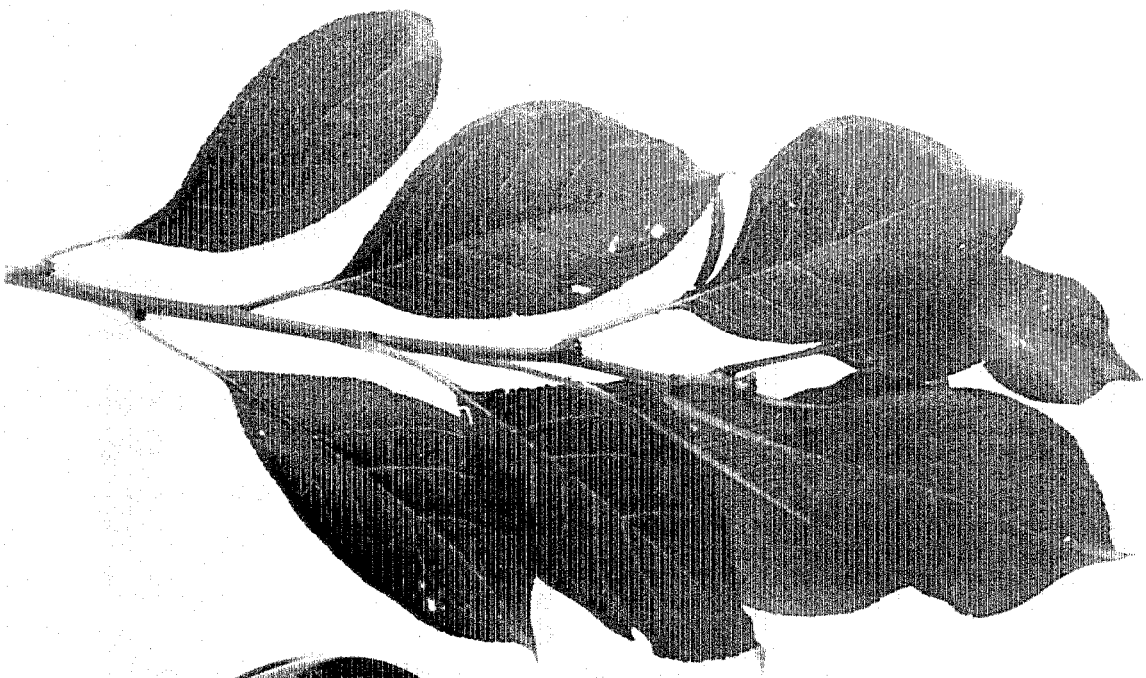
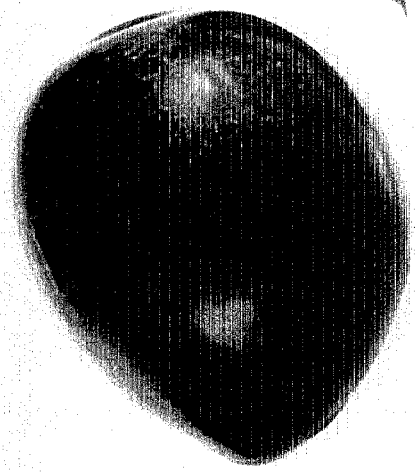
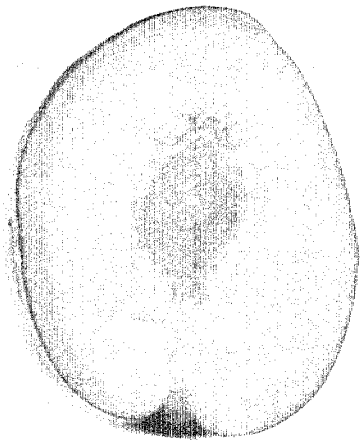
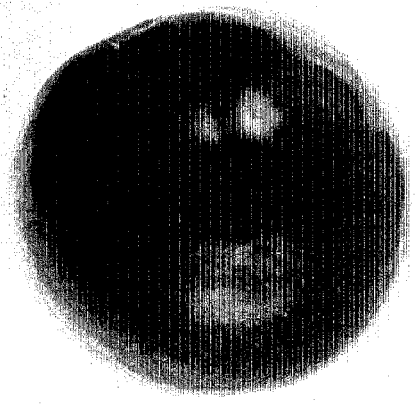
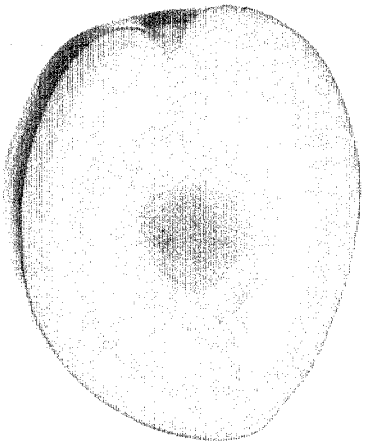

* * * * *